United States Patent
Markle et al.

(10) Patent No.: US 6,639,663 B1
(45) Date of Patent: *Oct. 28, 2003

(54) METHOD AND APPARATUS FOR DETECTING PROCESSING FAULTS USING SCATTEROMETRY MEASUREMENTS

(75) Inventors: Richard J. Markle, Austin, TX (US); Matthew A. Purdy, Austin, TX (US)

(73) Assignee: Advanced Micro Devices, Inc., Austin, TX (US)

( * ) Notice: Subject to any disclaimer, the term of this patent is extended or adjusted under 35 U.S.C. 154(b) by 203 days.

This patent is subject to a terminal disclaimer.

(21) Appl. No.: 09/863,562

(22) Filed: May 23, 2001

(51) Int. Cl.$^7$ .............................................. G01N 21/00
(52) U.S. Cl. ........................ 356/237.4; 356/237.5; 356/394; 250/559.09
(58) Field of Search ................ 356/237.1–237.6, 356/394; 250/559.09, 559.16, 559.45, 225; 438/5–18, 695; 382/149; 451/6

(56) References Cited

U.S. PATENT DOCUMENTS

| | | | |
|---|---|---|---|
| 5,393,624 A | | 2/1995 | Ushijima ...................... 430/30 |
| 5,867,276 A | | 2/1999 | McNeil et al. ............... 356/445 |
| 5,880,838 A | | 3/1999 | Marx et al. ................... 356/351 |
| 5,886,909 A | * | 3/1999 | Milor et al. ............. 356/237.1 |
| 6,051,348 A | | 4/2000 | Marinaro et al. ............. 430/30 |
| 6,067,154 A | * | 5/2000 | Hossain et al. .......... 356/237.2 |
| 6,067,163 A | * | 5/2000 | Guldi et al. ................. 356/394 |
| 6,192,287 B1 | * | 2/2001 | Solomon et al. ............ 382/149 |
| 6,222,936 B1 | * | 4/2001 | Phan et al. ................... 382/149 |
| 6,232,134 B1 | * | 5/2001 | Farber et al. ................... 438/9 |
| 6,245,584 B1 | | 6/2001 | Marinaro et al. ............. 438/14 |
| 6,433,878 B1 | | 8/2002 | Niu et al. .................... 356/603 |
| 6,451,700 B1 | * | 9/2002 | Stirton et al. ............... 438/695 |
| 6,458,605 B1 | * | 10/2002 | Sirton ............................ 438/7 |
| 6,464,563 B1 | * | 10/2002 | Lensing .......................... 451/6 |
| 6,479,309 B1 | * | 11/2002 | Wright ......................... 438/16 |
| 2002/0135781 A1 | | 9/2002 | Singh et al. ................. 356/601 |

FOREIGN PATENT DOCUMENTS

JP        448 583        *  2/1995

OTHER PUBLICATIONS

Bishop et al., "Use of Scatterometry for resist process control," *SPIE Integrated Circuit Metrology, Inspection and Process Control*, 1673:441–452, 1992.

Hickman et al., "Use of diffracted light from latent images to improve lithography control," *SPIE Integrated Circuit Metrology, Inspection and Process Control*, 1464:245–257, 1991.

McNeil et al., "Scatterometry applied to microelectronics processing—Part 1," *Solid State Technology*, 37(3):29–56, 1993.

Miller and Mellicamp, "Development of an end–point detection procedure for the post–exposure bake process," *Integrated circuit metrology, inspection, and process control IX: Feb., 20–22, 1995, Santa Clara, California, SPIE Integrated Circuit Metrology, Inspection and Process Control*, 2439:78–88, 1995.

(List continued on next page.)

*Primary Examiner*—Frank G. Font
*Assistant Examiner*—Sang H. Nguyen
(74) *Attorney, Agent, or Firm*—Williams Morgan & Amerson, P.C.

(57) ABSTRACT

A method for characterizing a misprocessed wafer includes providing a wafer having a grating structure; illuminating at least a portion of the grating structure; measuring light reflected from the grating structure to generate a reflection profile; and characterizing a misprocessed condition of the wafer based on the reflection profile. A metrology tool adapted to receive a wafer having a grating structure includes a light source, a detector, and a data processing unit. The light source is adapted to illuminate at least a portion of the grating structure. The detector is adapted to measure light reflected from the grating structure to generate a reflection profile. The data processing unit is adapted to characterize a misprocessed condition of the wafer based on the reflection profile.

14 Claims, 5 Drawing Sheets-

OTHER PUBLICATIONS

Milner et al., "Latent image exposure monitor using scatterometry," *SPIE Integrated Circuit Metrology, Inspection and Process Control*, 1673:274–283, 1992.

Prins et al., "Scatterometric sensor for PEB process control," *Metrology, inspection, and process control for microlithogtaphy, X: Mar., 11–13, 1996, Santa Clara, California, SPIE Integrated Circuit Metrology, Inspection and Process Control*,2725:710–719, 1996.

Raymond et al., "Multiparameter process metrology using scatterometry," In: *Optical characterization techniques for high–performance microelectronic device manufacturing II, SPIE—The International Society for Optical Engineering*, 2638:84–93, Austin, Texas, Oct. 25–26, 1995.

Raymond et al., "Scatterometric sensor for lithography," In: *Manufacturing process control for microelectronic devices and circuits, SPIE—The International Society for Optical Engineering*, 2336:37–49, Austin, Texas, Oct. 20–21, 1994.

Sturtevant et al., "Post–exposure bake as a process–control parameter for chemically–amplified photoresist," *Metrology, inspection, and process control for microlithogtaphy, VII:2–4, Mar., 1993, Santa Jose, California, SPIE Integrated Circuit Metrology, Inspection and Process Control*, vol. 1926, 1993.

Sturtevant et al., "Use of scatterometric latent image detector in closed loop feedback control of linewidth," *SPIE Integrated Circuit Metrology, Inspection and Process Control*, 2196:352–359, 1994.

* cited by examiner

METHOD AND APPARATUS FOR DETECTING PROCESSING FAULTS USING SCATTEROMETRY MEASUREMENTS

BACKGROUND OF THE INVENTION

1. Field of the Invention

This invention relates generally to the field of semiconductor device manufacturing and, more particularly, to a method and apparatus for detecting processing faults using scatterometry measurements.

2. Description of the Related Art

There is a constant drive within the semiconductor industry to increase the quality, reliability and throughput of integrated circuit devices, e.g., microprocessors, memory devices, and the like. This drive is fueled by consumer demands for higher quality computers and electronic devices that operate more reliably. These demands have resulted in a continual improvement in the manufacture of semiconductor devices, e.g., transistors, as well as in the manufacture of integrated circuit devices incorporating such transistors. Additionally, reducing the defects in the manufacture of the components of a typical transistor also lowers the overall cost per transistor as well as the cost of integrated circuit devices incorporating such transistors.

The technologies underlying semiconductor processing tools have attracted increased attention over the last several years, resulting in substantial refinements. However, despite the advances made in this area, many of the processing tools that are currently commercially available suffer certain deficiencies. In particular, such tools often lack advanced process data monitoring capabilities, such as the ability to provide historical parametric data in a user-friendly format, as well as event logging, real-time graphical display of both current processing parameters and the processing parameters of the entire run, and remote, i.e., local site and worldwide, monitoring. These deficiencies can engender nonoptimal control of critical processing parameters, such as throughput, accuracy, stability and repeatability, processing temperatures, mechanical tool parameters, and the like. This variability manifests itself as within-run disparities, run-to-run disparities and tool-to-tool disparities that can propagate into deviations in product quality and performance, whereas an ideal monitoring and diagnostics system for such tools would provide a means of monitoring this variability, as well as providing means for optimizing control of critical parameters.

Semiconductor devices are manufactured from wafers of a substrate material. Layers of materials are added, removed, and/or treated during fabrication to create the electrical circuits that make up the device. The fabrication essentially comprises four basic operations. Although there are only four basic operations, they can be combined in hundreds of different ways, depending upon the particular fabrication process.

The four operations typically used in the manufacture of semiconductor devices are:

layering, or adding thin layers of various materials to a wafer from which a semiconductor device is produced;

patterning, or removing selected portions of added layers;

doping, or placing specific amounts of dopants in the wafer surface through openings in the added layers; and heat treatment, or heating and cooling the materials to produce desired effects in the processed wafer.

Occasionally, during the fabrication process, one or more process steps are omitted on a production wafer. Such omissions may be due to an error in the fabrication facility automated work flow system (e.g., a database or control script error), a tool failure, or an operator error. If the omitted process steps occur early during the fabrication process, it is not uncommon for the faulty wafer to undergo many subsequent steps prior to the faulty fabrication being identified. Often such identification occurs much further down the processing line, such as during the performance of electrical tests on the devices formed on the wafer. As a result, many resources, such as materials, tool time, operator time, etc., are wasted until the faulty fabrication can be identified.

The present invention is directed to overcoming, or at least reducing the effects of, one or more of the problems set forth above.

SUMMARY OF THE INVENTION

One aspect of the present invention is seen in a method for characterizing a misprocessed wafer. The method includes providing a wafer having a grating structure; illuminating at least a portion of the grating structure; measuring light reflected from the grating structure to generate a reflection profile; and characterizing a misprocessed condition of the wafer based on the reflection profile.

Another aspect of the present invention is seen in a metrology tool adapted to receive a wafer having a grating structure. The metrology tool includes a light source, a detector, and a data processing unit. The light source is adapted to illuminate at least a portion of the grating structure. The detector is adapted to measure light reflected from the grating structure to generate a reflection profile. The data processing unit is adapted to characterize a misprocessed condition of the wafer based on the reflection profile.

BRIEF DESCRIPTION OF THE DRAWINGS

The invention may be understood by reference to the following description taken in conjunction with the accompanying drawings, in which like reference numerals identify like elements, and in which.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Figure 1:
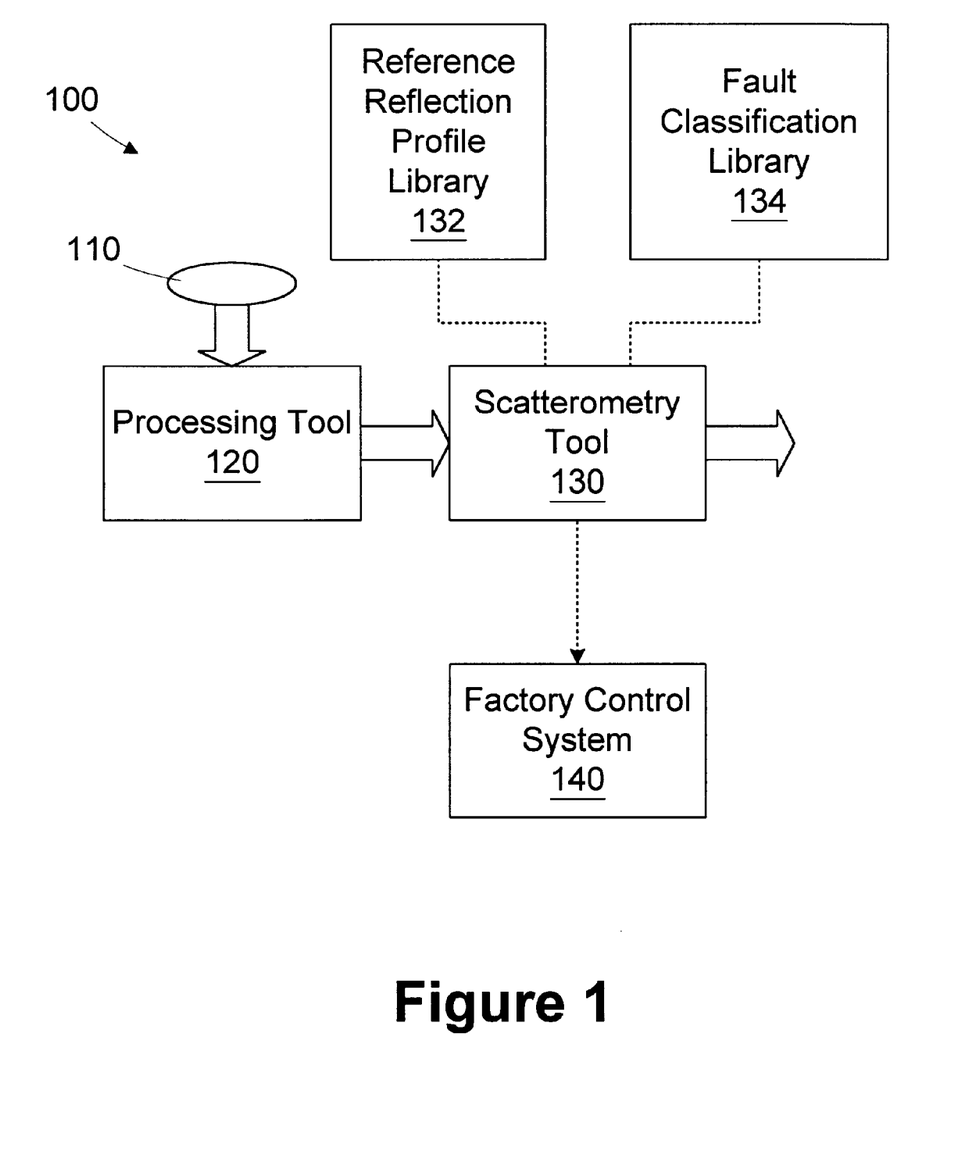
FIG. 1 is a simplified diagram of an illustrative processing line for processing wafers in accordance with one illustrative embodiment of the present invention.

Referring now to the Figures, and particularly to FIG. 1, a simplified block diagram of a processing line 100 useful for processing wafers 110 is provided. The processing line 100 includes a processing tool 120 for performing a process task on the wafer 110 to form various features of an active semiconductor device. For example, the processing tool 120 may be an etch tool used to etch a transistor gate electrode on the wafer 110, a deposition tool for forming a process layer on the wafer 110, a polishing tool adapted to planarize a process layer on the wafer 110, etc. A scatterometry tool 130 is provided for measuring a characteristic of the wafer 110 for evaluating the performance of the processing tool 120. The operation of the scatterometry tool 130 is described in greater detail below. In general, the scatterometry tool 130 includes optical hardware, such as an ellipsometer or reflectometer, and a data processing unit loaded with a scatterometry software application for processing data collected by the optical hardware. For example, the optical hardware may include a model OP5230 or OP5240 with a spectroscopic ellipsometer offered by Therma-Wave, Inc. of Freemont Calif. The data processing unit may comprise a profile application server manufactured by Timbre Technologies, a subsidiary of Tokyo Electron Limited, Inc. of Kumamoto, Japan and distributed by Therma-Wave, Inc.

In standard mode of operation, the scatterometry tool 130 evaluates a characteristic of a feature formed on the wafer 110. For example, the scatterometry tool 130 may measure a profile of the transistor gate electrode, step height of a trench feature, conformality of a process layer formed on the wafer, planarity of a polished process layer, dishing of a polished layer, etc. In general, the scatterometry tool 130 measures features formed on the wafer 110 by measuring light reflected from a grating structure, such as a group of transistor gate electrodes, and comparing the measured reflection profile to a library of reference reflection M) profiles 132. For example, scatterometry libraries are commercially available from Timbre Technologies, Inc. The scatterometry tool 130 may also compare the measured reflection profile to a target reflection profile stored in the reference reflection profile library 132. Each reference reflection profile has an associated characteristic. For example, in measuring gate electrodes, each reference reflection profile may have an associated gate electrode profile. Based on the comparison to the reference reflection profiles, the scatterometry tool 130 determines the corresponding characteristic, e.g., gate electrode profile, of the measured wafer 110.

In some instances, the scatterometry tool 130 may not find a reference reflection profile that is sufficiently close to the measured reflection profile, or the measured reflection profile may be significantly different than the target reflection profile, such that it is unlikely that the measured wafer 110 was processed in the expected manner. For example, one of the expected process layers may be missing, or the process layer may have been constructed from the wrong material. Upon failing to match the measured reflection profile to a reference reflection profile, the scatterometry tool 130 shifts to a fault classification mode. The scatterometry tool 130 then compares the measured reflection profile to a fault classification library 134 to attempt to characterize the processing fault. The fault classification library 134 includes a library of misprocessed reflection profiles associated with known processing faults. For example, the fault classification library 134 may include misprocessed reflection profiles for features that were formed with missing, extra, or incorrect process layers.

Figure 2A:
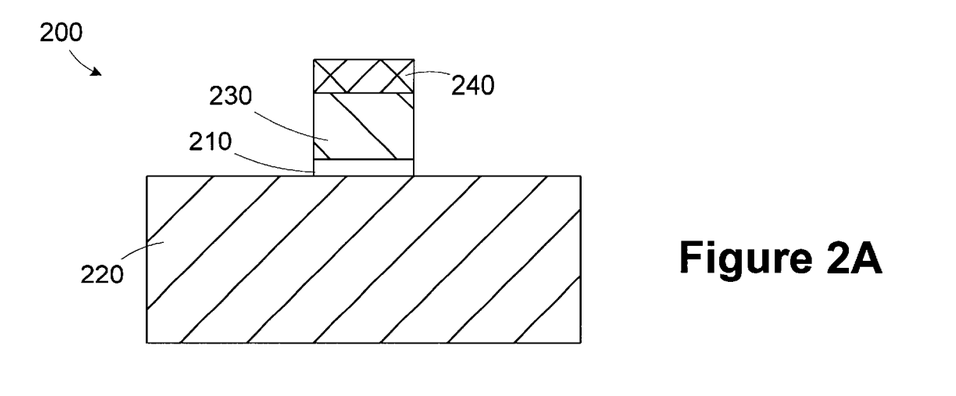
FIGS. 2A, 2B, and 2C are cross section views of exemplary semiconductor devices.

Referring to FIG. 2A, a cross-section view of a transistor gate stack 200 is provided. The transistor gate stack 200 of FIG. 2A represents an expected configuration for the features formed by the processing line 100. The transistor gate stack 200 includes a gate insulating layer 210 formed over a substrate 220. A polysilicon layer 230 is formed over the gate insulating layer 210, and an antireflective coating (ARC) layer 240, such as silicon oxynitride (SiON), is formed over the polysilicon layer 230. The ARC layer 240 is typically used to enhance photolithography processes used in forming a photoresist pattern and etching the transistor gate stack 200.

Figure 2B:
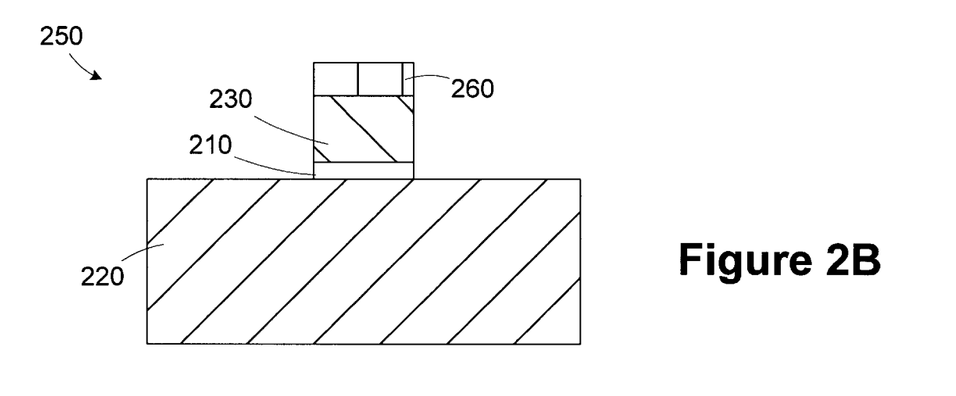
Figure 2C:
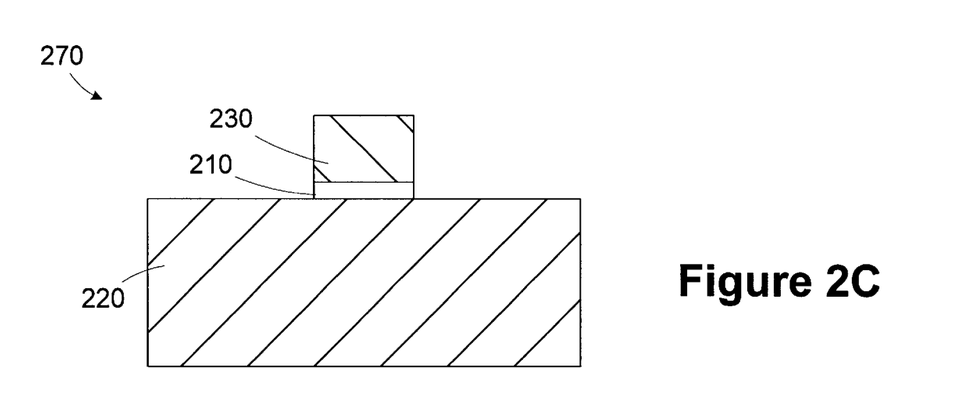

FIG. 2B illustrates a cross-section view of a misprocessed transistor gate stack 250, wherein the wrong material was used for the formation of an ARC layer 260. For example, silicon nitride ($Si_3N_4$) may have been errantly used instead of the desired SiON. Typically, the same type of deposition tools are used to form both types of layers. FIG. 2C illustrates a cross-section view of a misprocessed transistor gate stack 270, wherein the ARC layer 240 was omitted.

Figure 3:
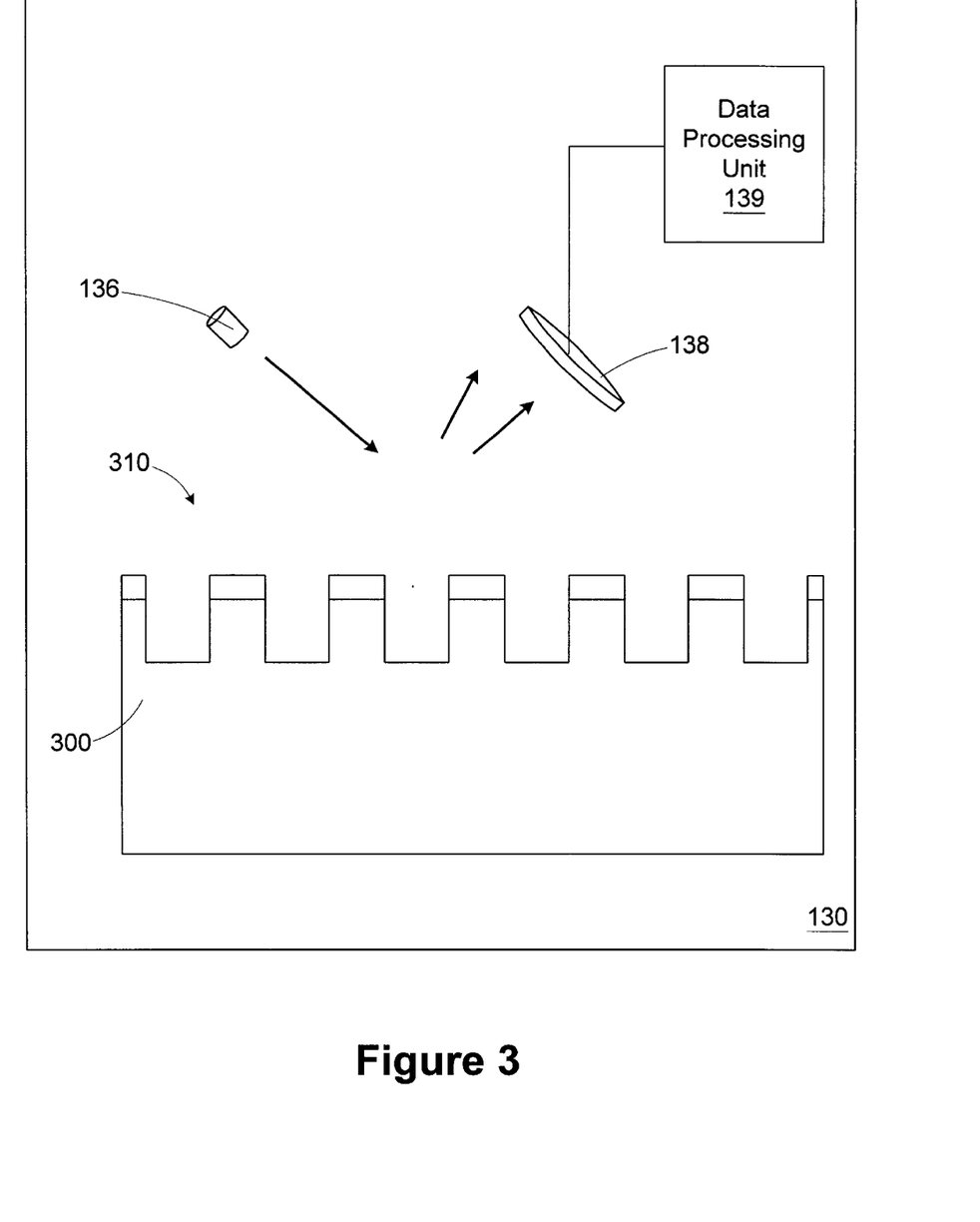
FIG. 3 is a simplified view of the scatterometry tool of FIG. 1 loaded with a wafer including a grating structure.

The operation of the scatterometry tool is now described in greater detail with reference to FIG. 3. For purposes of illustration, the operation of the scatterometry tool is described as it may be applied to measuring characteristics of the gate stacks 200, 250, 270 shown in FIGS. 2A, 2b, and 2C. The scatterometry tool 130 is loaded with a wafer 300 having a grating structure 310. The grating structure 310 may be features formed in a production device on the wafer 300 (e.g., gate electrodes, shallow trench isolation structures, interconnection trenches), or alternatively, the grating structure 310 may be a test structure having dimensions and construction materials similar to a production device. The scatterometry tool 130, includes a light source 136 and a detector 138 positioned proximate the grating structure 310. The light source 136 of the scatterometry tool 130 illuminates at least a portion of the grating structure 310, and the detector 138 takes optical measurements, such as intensity or phase, of the reflected light. A data processing unit 139 receives the optical measurements from the detector 136 and processes the data to determine a characteristic of the grating structure 310 (e.g., transistor gate electrode profile, step height, conformality, planarity, dishing, etc.).

Although the invention is described using a scatterometry tool 130 designed to measure reflected light intensity or phase, other measurement tools, such as an ellipsometer, a reflectometer, a spectrometer, or some other light measuring device may be used. The scatterometry tool 130 may use monochromatic light, white light, or some other wavelength or combinations of wavelengths, depending on the specific implementation. The angle of incidence of the light may also vary, depending on the specific implementation. The light analyzed by the scatterometry tool 130 typically includes a reflected component (i.e., incident angle equals reflected angle) and a refracted component (i.e., incident angle does not equal the reflected angle). For purposes of discussion here, the term "reflected" light is meant to encompass both components.

Variations in the characteristics of the grating structure 310 cause changes in the reflection profile (e.g., intensity vs.

wavelength—tan(δ), phase vs. wavelength—sin(ψ), where δ and ψ are common scatterometry outputs known to those of ordinary skill in the art) measured by the scatterometry tool 130. The particular reflection profile expected for any structure depends on the specific geometry of the grating structure 310 and the parameters of the measurement technique employed by the scatterometry tool 130 (e.g., light bandwidth, angle of incidence, etc.). The profiles in the reference reflection profile library 132 and the fault classification library 134 are typically calculated theoretically by employing Maxwell's equations based on the topology and geometry of the grating structure 310. The process for generating reference reflection profiles is well known to those of ordinary skill in the art, and accordingly, it is not described in greater detail herein for clarity and so as not to obscure the invention. The profiles in the reference reflection profile library 132 and the fault classification library 134 may also be generated empirically by measuring reflection profiles of sample wafers and subsequently characterizing step the measured wafers by some other destructive or non-destructive examination technique.

Figure 4A:
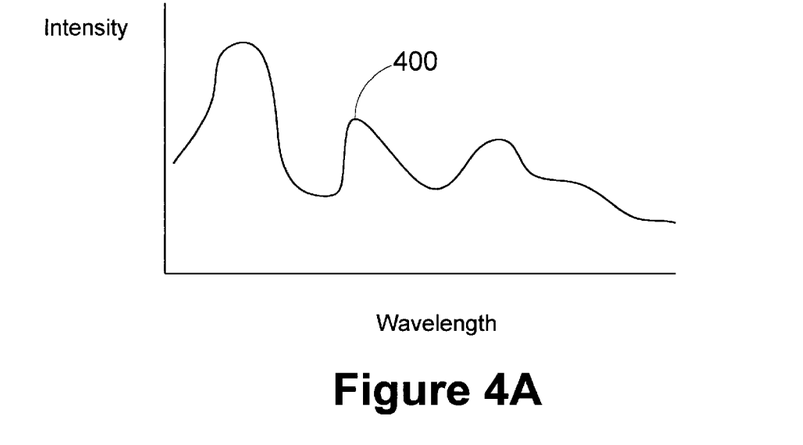
FIGS. 4A, 4B, and 4C illustrate exemplary scatterometry reflection profiles used to characterize processing faults on the wafer measured in the scatterometry tool of FIG. 3.
Figure 4B:
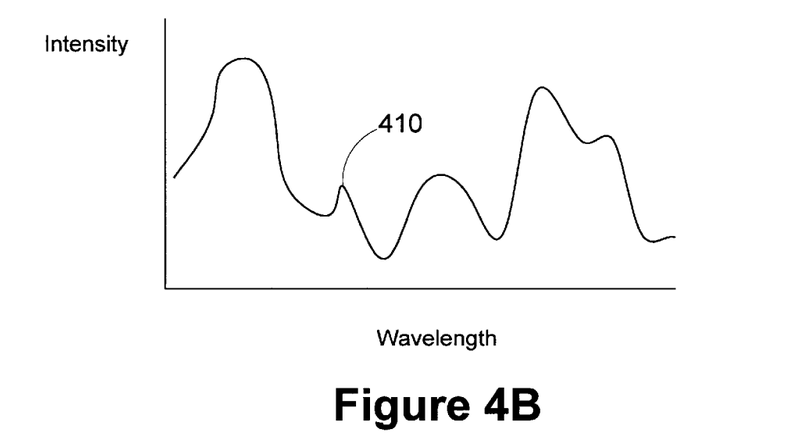
Figure 4C:
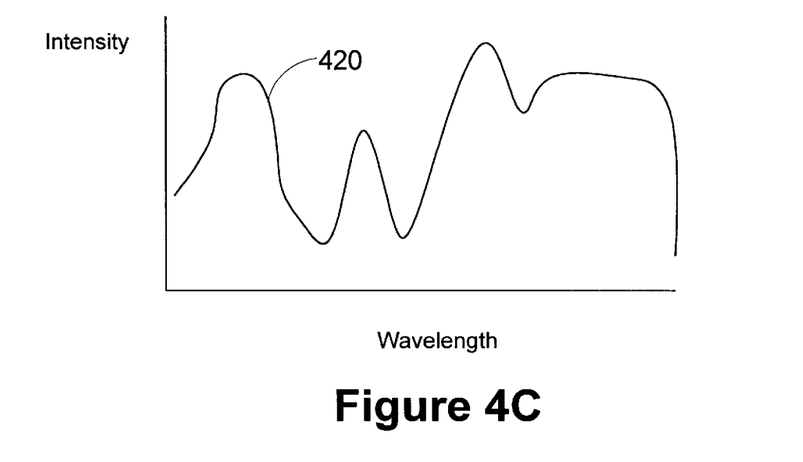

FIGS. 4A, 4B, and 4C illustrate exemplary reflection profiles 400, 410, 420. The reflection profile 400 represents an expected or target reflection profile of the properly formed gate stack 200 of FIG. 2A, and may be contained within the reference reflection profile library 132 of FIG. 1. In the measurement mode of operation, the scatterometry tool 130 measures the reflection profile of the grating structure 310 and attempts to match the measured reflection profile to one of the profiles in the reference reflection profile library 132 to characterize the grating structure 310 (e.g., tapered or re-entrant gate electrode profile). Techniques for matching the measured reflection profile to the closest reference reflection profile are well known to those of ordinary skill in the art, so they are not described in greater detail herein.

If the grating structure 310 has been misprocessed, such as shown in FIGS. 2B and 2C, the measured reflection profile will not be sufficiently close to any of the profiles in the reference reflection profile library 132 to indicate a match (i.e., the least squared difference between the measured reflection profile and the reference reflection profiles will exceed a predetermined threshold, indicating a bad fit). After failing to match the measured reflection profile with one of the profiles in the reference reflection profile library 132, the data processing unit 139 switches to the fault classification library 134 and attempts to match the measured reflection profile with one of the misprocessed reflection profiles. For example, the reflection profiles 410 and 420 of FIGS. 4B and 4C may represent the reflection profiles of the misprocessed devices of FIGS. 2B and 2C. The data processing unit 139 matches the measured reflection profile with the misprocessed profiles in the fault classification library 134 to classify the processing fault. In evaluating the measured reflection profile against the misprocessed reflection profiles in the fault classification library 134, that data processing unit 139 may use a least squared difference technique for determining the closest misprocessed reflection profile.

Upon identifying a misprocessed wafer 300, the scatterometry tool 130 may send an alert message to an operator of the processing tool 110, a manager of the processing line 100, or to a factory control system 140 (shown in FIG. 1) responsible for controlling the operations of the processing line 100. The factory control system 140 may log the processing fault and schedule the wafer 300 to be reworked or scrapped, depending on the specific nature of the misprocessing. The information about the specific type of misprocessing can be used to correct the problem introduced by the previous process steps to prevent recurrence.

Figure 5:
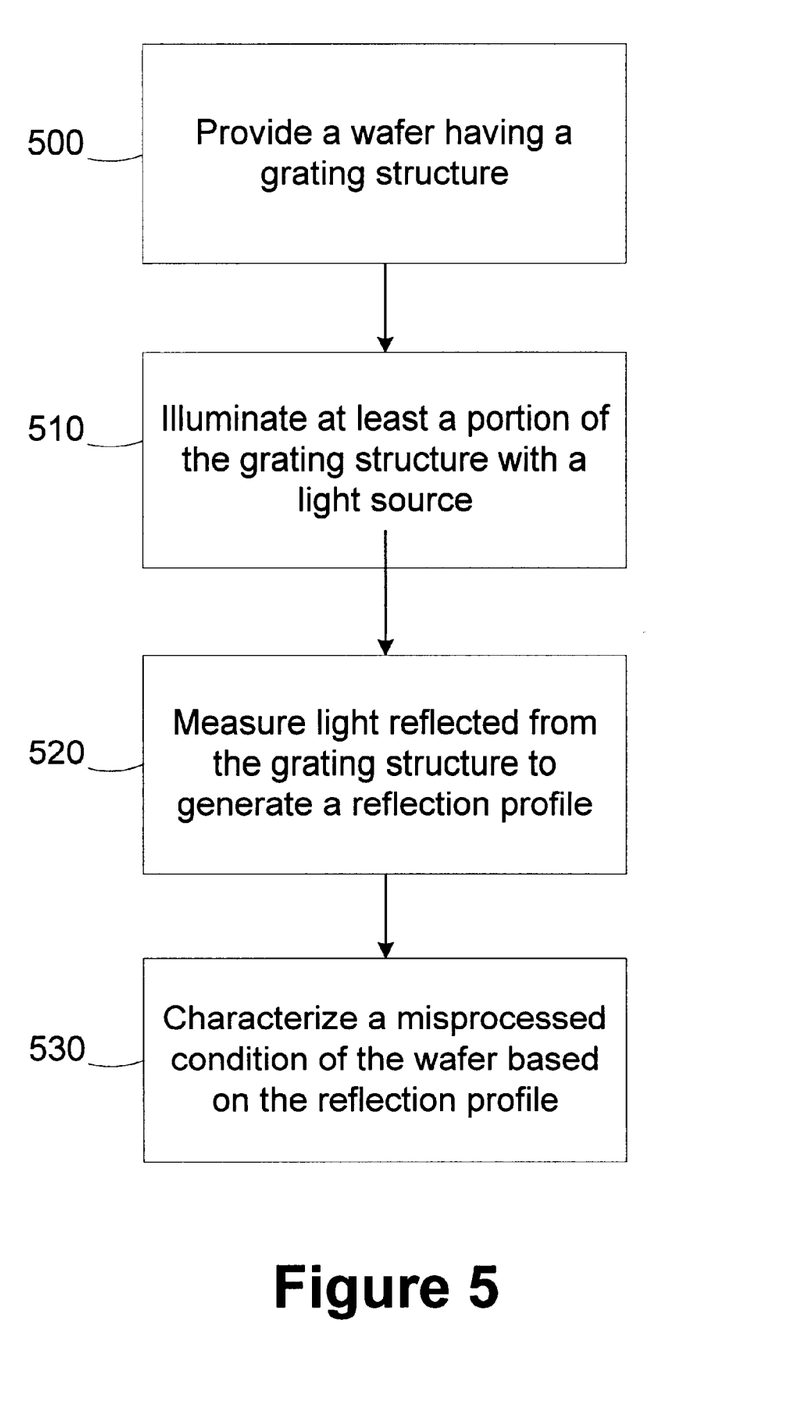
FIG. 5 is a simplified flow diagram of a method for detecting processing faults using scatterometry measurements in accordance with another illustrative embodiment of the present invention.

Turning now to FIG. 5, a simplified flow diagram of a method for detecting processing faults using scatterometry measurements in accordance with another illustrative embodiment of the present invention is provided. In block 500, a wafer having a grating structure is provided. In block 510, at least a portion of the grating structure is illuminated.

In block 520, light reflected from the grating structure is measured to generate a reflection profile. In block 530, a misprocessed condition of the wafer is characterized based on the reflection profile.

Detecting and characterizing misprocessed wafers, as described above, allows misprocessed wafers to be identified prior to the expenditure of unnecessary resources required to continue processing the wafer. Such resource conservation improves the efficiency, and thus, the profitability, of the processing line 100. Information about the specific type of misprocessing can be provided to allow correction of the problem in previous process steps to prevent repetitions of the misprocessing.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method for characterizing a misprocessed wafer, comprising:

providing a wafer having a grating structure;

illuminating at least a portion of the grating structure;

measuring light reflected from the grating structure to generate a reflection profile;

comparing the generated reflection profile to a library of reference reflection profiles, each reference reflection profile having an associated characteristic;

determining if the generated reflection profile correlates with any of the reference reflection profiles;

identifying a misprocessed condition of the wafer in response to the generated reflection profile not correlating with any of the reference reflection profiles;

comparing the generated reflection profile to a fault classification library of reflection profiles, each reference reflection profile having an associated processing fault;

selecting a reflection profile closest to the generated reflection profile; and characterizing the misprocessed condition of the wafer based on the processing fault associated with the selected reflection profile.

2. The method of claim 1, wherein generating the reflection profile comprises generating the reflection profile based on at least one of intensity and phase of the reflected light.

3. The method of claim 1, wherein providing the wafer comprises providing the wafer having the grating structure formed in a test structure on the wafer.

4. The method of claim 1, wherein providing the wafer comprises providing the wafer having the grating struture formed in a production device on the wafer.

5. The method of claim 1, wherein characterizing the misprocessed condition comprises characterizing the misprocessed condition as one of a missing process layer, an extra process layer, and a process layer material error.

6. A method for characterizing a misprocessed wafer, comprising:

provid­ing a wafer having a grating structure;

illuminating at least a portion of the grating structure;

measuring light reflected from the grating structure to generate a reflection profile;

comparing the generated reflection profile to a target reflection profile to determine a characteristic of the grating struture based on the comparison of the generated reflection profile and the target reflection profile;

identifying a misprocessed condition of the wafer in response to the generated reflection profile being dissimilar to the target reflection profile;

comparing the generated reflection profile to a fault classification library of reflection profiles, each reference reflection profile having an associated processing fault;

selecting a reflection profile closest to the generated reflection profile; and characterizing the misprocessed condition of the wafer based on the processing fault associated with the selected reflection profile.

7. A metrology tool adapted to receive a wafer having a grating structure, comprising:

a light source adapted to illuminate at least a portion of the grating structure;

a detector adapted to measure light reflected from the grating structure to generate a reflection profile; and a data processing unit adapted to compare the generated reflection profile to a library of reference reflection profiles, each reference reflection profile having an associated characteristic, determine if the generated reflection profile correlates with any of the reference reflection profiles, identify a misprocessed condition of the wafer in response to the generated reflection profile not correlating with any of the reference reflection profiles, compare the generated reflection profile to a fault classification library of reflection profiles, each reference reflection profile having an associated processing fault, select a reflection profile closest to the generated reflection profile, and characterize the misprocessed condition of the wafer based on the processing fault associated with the selected reflection profile.

8. The metrology tool of claim 7, wherein the generated reflection profile is based on at least one of intensity and phase of the reflected light.

9. The metrology tool of claim 7, wherein the grating structure is formed in a test structure on the wafer.

10. The metrology tool of claim 7, wherein the grating structure is formed in a production device on the wafer.

11. The metrology tool of claim 7, wherein the data processing unit is further adapted to characterize the misprocessed condition as one of a missing process layer, an extra process layer, and a process layer material error.

12. A metrology tool adapted to receive a wafer having a grating structure, comprising:

a light source adapted to illuminate at least a portion of the granting structure;

a detector adapted to measure light reflected from the grating structure to generated a reflection profile; and a data processing unit adapted to compare the generated reflection profile to a target reflection profile to determine a characteristic of the grating structure based on the comparison of the generated reflection profile and the target reflection profile, identify a misprocessed condition of the wafer in response to the generated reflection profile being dissimilar to the target reflection profile, compare the generated reflection profile to a fault classification library of reflection profiles, each reference reflection profile having an associated processing fault, select a reflection profile closest to the generated reflection profile, and characterize the misprocessed condition of the wafer based on the processing fault associated with the selected reflection profile.

13. A metrology tool adapted to receive a wafer having a grating structure, comprising:

means for illuminating at least a portion of the grating structure;

means for measuring light reflected from the grating structure to generate a reflection profile;

means for comparing the generated reflection profile to a library of reference reflection profiles, each reference reflection profile having an associated characteristic;

means for determining if the generated reflection profile correlates with any of the reference reflection profiles;

means for identifying a misprocessed condition of the wafer in response to the generated reflection profile not correlating with any of the reference reflection profiles;

means for comparing the generated reflection profile to a fault classification library of reflection profiles, each reference reflection profile having an associated processing fault;

means for selecting a reflection profile closest to the generated reflection profile; and means for characterizing a misprocessed condition of the wafer based on the processing fault associated with the selected reflection profile.

14. A metrology tool adapted to receive a wafer having a grating structure, comprising:

means for illuminating at least a portion of the grating structure;

means for measuring light reflected from the grating structure to generate a reflection profile;

means for comparing the generated reflection profile to a target reflection profile to determine a characteristic of the grating structure based on the comparison of the generated reflection profile and the target reflection profile;

means for identifying a misprocessed condition of the wafer in response to the generated reflection profile being dissimilar to the target reflection profile;

means for comparing the generated reflection profile to a fault classification library of reflection profiles, each reference reflection profile having an associated processing fault;

means for selecting a reflection profile closest to the generated reflection profile; and means for characterizing the misprocessed condition of the wafer based on the processing fault associated with the select reflection profile.

* * * * *